(12) United States Patent
Liu et al.

(10) Patent No.: US 9,510,908 B2
(45) Date of Patent: Dec. 6, 2016

(54) SEMICONDUCTOR LASER SYSTEM FOR LASER MEDICAL COSMETOLOGY

(71) Applicant: Xi'An Focuslight Technologies Co., Ltd., Xi'an, Shanxi (CN)

(72) Inventors: Xingsheng Liu, Xi'an (CN); Ye Dai, Xi'an (CN); Yao Sun, Xi'an (CN); Di Wu, Xi'an (CN); Hengjun Zong, Xi'an (CN); Lishun Tong, Xi'an (CN); Lei Cai, Xi'an (CN)

(73) Assignee: Focuslight Technologies Inc, Shaanxi Xi'an (CN)

( * ) Notice: Subject to any disclaimer, the term of this patent is extended or adjusted under 35 U.S.C. 154(b) by 64 days.

(21) Appl. No.: 14/646,439

(22) PCT Filed: Nov. 21, 2013

(86) PCT No.: PCT/CN2013/087603
§ 371 (c)(1),
(2) Date: May 21, 2015

(87) PCT Pub. No.: WO2014/079375
PCT Pub. Date: May 30, 2014

(65) Prior Publication Data
US 2015/0289934 A1     Oct. 15, 2015

(30) Foreign Application Priority Data

Nov. 22, 2012  (CN) .......................... 2012 1 0479918
Nov. 22, 2012  (CN) .......................... 2012 1 0479919
(Continued)

(51) Int. Cl.
*A61B 18/20*     (2006.01)
*H01S 5/00*      (2006.01)
(Continued)

(52) U.S. Cl.
CPC ............. *A61B 18/203* (2013.01); *H01S 5/005* (2013.01); *H01S 5/02415* (2013.01);
(Continued)

(58) Field of Classification Search
CPC .................. A61B 18/203; A61B 2018/00005; H01S 5/4025; H01S 5/005; H01S 5/02446; H01S 5/02415; H01S 5/02407; H01S 5/02438; H01S 5/4031
See application file for complete search history.

(56) References Cited

FOREIGN PATENT DOCUMENTS

CN          1452465     * 10/2003    ............. A61B 18/20

\* cited by examiner

*Primary Examiner* — Gary Jackson
*Assistant Examiner* — Scott T Luan
(74) *Attorney, Agent, or Firm* — Na Xu; IPro, PLLC

(57) ABSTRACT

A semiconductor laser system for laser medical cosmetology, comprising a semiconductor laser array (1), an optical waveguide (2), a boss-shaped transparent contact window (3) located at the light outlet end of the optical waveguide (2), and a refrigeration block (4) for conduction cooling of the contact window (3); the refrigeration block (4) consists of a base portion and a hollow head above the base portion; the front part of the hollow head presses against and is tightly fastened to the whole side wall of the contact window (3); the light outlet end of the optical waveguide (2) is located in the cavity of the hollow head, and has a gap between the waveguide and the inner wall of the hollow head; a thermoelectric semiconductor refrigerator (5) is disposed below the base portion of the refrigeration block (4); a first water supply block (6) is disposed below the thermoelectric semiconductor refrigerator (5); and a second water supply block (16) for heat dissipation is installed in the semiconductor laser array (1). The system employs a unique refrigeration structure design so as to cause the temperature
(Continued)

of the face of the working end in direct contact with skin to approach the freezing point, and the structure is compact and stable.

19 Claims, 5 Drawing Sheets

(30)           Foreign Application Priority Data

Nov. 22, 2012   (CN) .......................... 2012 1 0480040
   Nov. 22, 2012   (CN) .......................... 2012 1 0480076
   Nov. 22, 2012   (CN) .......................... 2012 1 0480078
   Nov. 22, 2012   (CN) .......................... 2012 1 0480080

(51)   Int. Cl.
      *H01S 5/024*        (2006.01)
      *H01S 5/40*         (2006.01)
      *A61B 18/00*      (2006.01)

(52)   U.S. Cl.
      CPC ........ *H01S 5/02446* (2013.01); *H01S 5/4025* (2013.01); *A61B 2018/00005* (2013.01); *H01S 5/02407* (2013.01); *H01S 5/02438* (2013.01); *H01S 5/4031* (2013.01)

SEMICONDUCTOR LASER SYSTEM FOR LASER MEDICAL COSMETOLOGY

FIELD OF THE INVENTION

The invention relates to the use of a semiconductor laser, and more particularly to a semiconductor laser system for medical cosmetology.

BACKGROUND OF THE INVENTION

As an important application field of laser, laser medical treatment has developed quickly in recent years and gradually matured. Featuring small size, light weight, long service life, low power consumption, broad wavelength coverage, etc., semiconductor lasers are particularly suitable for the manufacturing of medical facilities.

Typical laser hair removal facilities include ruby laser (wavelength of 694 nm), alexandrite laser (wavelength of 755 nm), semiconductor laser (wavelength of 810 nm), and Q-switched Nd YAG laser (wavelength of 1064 nm), among which, the semiconductor laser has been proved as a safe and effective hair removal tool.

It is estimated that in 2010 there are about 5 million person times of laser hair removal surgery all over the world. Another important application of the semiconductor laser in the beauty field is to conduct skin renewal, that is, for wrinkle removal and skin rejuvenation. Laser is absorbed by moisture in the dermal collagen tissue to produce thermal effect, which stimulates the regeneration and remolding of collagen thereby smoothing and softening the skin, and providing the skin with elasticity. In addition, laser can also be used for treatment of dark, blue pigment lesions such as freckles, traumatic pigmentation, tattoo removal, eyebrow, eyeliner, and the like.

The most widely used thermal source in ophthalmology is the semiconductor laser, which can be used for treatment of refractory glaucoma, refractory intraocular hypertension after silicon oil injection, and photocoagulation and fixation of retina, and the like.

With the development and maturation of the semiconductor laser technology, the semiconductor laser exhibits more and more advantages and the application scope thereof is expanding rapidly, almost covering the application scopes of all other lasers. The semiconductor laser can not only make up for the shortcomings of difficult optical fiber transmission and inconvenient operation of a high energy $CO_2$ laser, but also make up for the shortcomings of low efficiency and inconvenient heat dissipation of a lamp pumped solid laser, so it is a potential mainstream medical laser.

Chinese Patent No. CN1452465 discloses a laser hair removal device. The device employs a semiconductor laser with an output power of 5 mW-1500 mW and a wavelength of 600 nm-1600 nm for hair removal. However, the system has a low output power, small spot size, and nonadjustable output wavelength, so the hair removal efficiency is very low.

SUMMARY OF THE INVENTION

In view of the above-described problems, it is one objective of the invention to provide a semiconductor laser system for medical cosmetology. The contact window of the system can contact skin directly.

To achieve the above objective, in accordance with one embodiment of the invention, there is provided a following basic technical solution.

A semiconductor laser system for medical cosmetology, comprising: a semiconductor laser array comprising a plurality of stacked semiconductor lasers, an optical waveguide disposed in front of a light emitting surface of the semiconductor laser array, a transparent convex contact window disposed in front of a light outlet end of the optical waveguide, a cooling block for conduction cooling of the contact window. The cooling block comprises a base and a hollow head located on the base; a forepart of the hollow head abuts against and tightly clasps side walls of the contact window; the light outlet end of the optical waveguide is located in a cavity of the hollow head, and a gap is provided between the light outlet end of the optical waveguide and an inner wall of the hollow head; a thermoelectric cooler is disposed below the base of the cooling block; a first water throughflow block is disposed below the thermoelectric cooler; and a second water throughflow block is disposed below the semiconductor laser array.

Based on the above-mentioned basic technical scheme, the present invention also provides the following optimized restrictions and improvements.

In a class of this embodiment, a hollow sleeve comprising a high reflection film-coated inner surface is fixed in the cavity of the hollow head; the hollow sleeve is connected to and fixed on the inner wall of the hollow head through point contact; a front end of the hollow sleeve abuts against a rear end surface of the contact window; the light outlet end of the optical waveguide is located in the hollow sleeve; and a gap is provided between the light outlet end of the optical waveguide and the hollow sleeve.

In a class of this embodiment, the hollow sleeve is made of copper and the high reflection film is gold-plated or silver-plated.

In a class of this embodiment, the optical waveguide is clamped and fixed using a pair of trough type fixed blocks disposed on the base of the cooling block or on the first water throughflow block; the pair of trough type fixed blocks are fixed by a through bolt; and a contact surface of the optical waveguide and the fixed blocks is provided with a flexible pad comprising a hollow center.

In a class of this embodiment, an insulation layer is disposed at a bottom of the semiconductor laser array, and the semiconductor laser array is fixed on the second water throughflow block via the insulation layer.

In a class of this embodiment, a thermal insulation cover is disposed to cover the base of the cooling block.

In a class of this embodiment, a guide channel is provided on the base of the cooling block and/or a surface of the first water throughflow block to guide excess water to discharge.

In a class of this embodiment, liquid cooling channels of the first water throughflow block and the second water throughflow block are connected in series or are independent from each other.

In a class of this embodiment, the optical waveguide as a whole is a cylinder, a frustum of a cone, a prism, or a frustum of a prism.

In a class of this embodiment, a space between the optical waveguide and the light emitting surface of the semiconductor laser array is between 0.5 and 5.0 mm.

In a class of this embodiment, the contact window is made of sapphire, K9 glass, quartz glass or diamond; the optical waveguide is made of sapphire, K9 glass, or diamond.

In a class of this embodiment, the contact window and the optical waveguide are an integrated structure of sapphire or diamond.

In a class of this embodiment, the cooling block is made of copper, aluminum, iron, gold-plated copper, gold-plated aluminum, stainless steel or diamond.

In a class of this embodiment, the first water throughflow block and the second water throughflow block are made of copper, aluminum, stainless steel, hard anodized aluminum or plastic.

In a class of this embodiment, the semiconductor lasers each comprise bar chips packaged on a heat sink, and the heat sink is a micro-channel heat sink, a macro-channel heat sink or a metal block; the bar chips comprise a single luminous point or a plurality of luminous points.

In a class of this embodiment, a collimating lens is disposed in front of the semiconductor lasers for fast axis collimation or for fast and slow axis collimation simultaneously.

In a class of this embodiment, the collimating lens is a miniature collimating lens disposed on a bar chip of each laser of the semiconductor laser array; or the collimating lens is an integrated structure disposed in front of the semiconductor laser array.

In a class of this embodiment, the optical waveguide is replaced by a pair of light barriers which are perpendicular to the slow axis and are plated with high-reflective films on inner sides thereof; the pair of light barriers is inserted and fixed on the base of the cooling block or a slot preset on the first water throughflow block; a light outlet end of the pair of light barriers is located in the cavity of the hollow head, and a gap is provided between the light outlet end of the light barriers and the inner wall of the hollow head; and the transparent convex contact window is disposed in front of the light outlet end of the light barriers.

In a class of this embodiment, the light barriers are made of gold-plated copper or silver-plated copper Advantages of the semiconductor laser system for medical cosmetology of the invention are summarized as follows.

1. The divergence angle of the bars along the fast axis in the semiconductor laser array is between 30 and 40 degrees, and the divergence angle along the slow axis is between 5 and 10 degrees. Employing the optical waveguide to transmit laser can restrict the divergence of the laser beams. The beams are reflected repeatedly in the optical waveguide to form uniform light spots in the end.

2. The coolers of the system feature unique, compact and stable structure, so that the temperature of the working end surface thereof adapted to direct contact with skin can be close to freezing point.

3. The thermoelectric coolers (TEC) are used as a cooling source to adjust the temperature of the cooling blocks and cool the contact window. The temperature of the contact window can drop to 5 degrees Celsuis (freezing point), thereby effectively alleviating the pain during treatment.

4. The water throughflow blocks are equipped with liquid cooling channels thereby having high heat dissipation efficiency. In addition, the water throughflow block below the thermoelectric coolers is in series connection to the liquid cooling channels of the semiconductor laser array, so that the cooling water paths of the semiconductor laser array and the thermoelectric coolers (TEC) are connected in series and communicate with one another via the water throughflow blocks, presenting a simple structure. As a result, the problem of the disconnection of branches of conventional parallel connected water paths is solved, the semiconductor laser can be cooled effectively, and the operation of the laser is stable and reliable.

5. The contact window is designed as a boss structure, which precludes the interference of auxiliaries such as cooling gel in the process of treatment, thereby ensuring the stable and reliable operation of the laser. The contact window is convenient for replacement, and close contacts the skin in use, so that the temperature of the contact site is close to freezing point, which effectively protects the skin from heat injury and alleviates pain, increases the treatment energy and improves the therapeutic effectiveness. In use, the contact window presses the skin and flattens the hair follicle, so that the absorption rate of the laser is increased by 30-40%.

6. The cooling block cools the contact window, so the temperature of the head of the cooling block should be low while that of the tail of the cooling block cannot be too low. If the temperature of the cooling block is too low, so is the temperature of the optical waveguide, and thus the condensation of moisture will occur at the light entrance of the optical waveguide, thereby polluting the semiconductor laser. To avoid the condensation of moisture and formation of excess water, a thermal insulation cover (layer) is disposed to cover the base of the cooling block.

7. The guide channel is provided on the water throughflow block (and the cooling block) so that excess water resulting from moisture condensation can be discharged, thereby avoiding the pollution of the laser semiconductor.

8. The hollow sleeve is fixed in the hollow head of the cooling block. The light emitting end of the optical waveguide is sleeved in the hollow sleeve. As a result, the potential leaked laser can only be reflected in the hollow sleeve and cannot act on the cooling block thereby ensuring the cooling of the contact part of skin (contact window). In addition, the hollow sleeve can also operate to tightly press the contact window.

9. The optical waveguide is clamped and fixed using fixed blocks. The contact site of the optical waveguide and the fixed block is a vertical plane or a horizontal plane, which benefits the stable clamping and fixation. The fixed blocks are disposed on the base of the cooling block and/or on the first water throughflow block.

10. The contact surface of the optical waveguide and the fixed blocks is provided with a pad. The two fixed blocks are fixed by a through bolt thereby preventing the fixed blocks from crushing the optical waveguide. The pad is provided with a hollow center and connects the fixed blocks with the optical waveguide, thereby diminishing the contact area between the pad and the optical waveguide, with no influence on the full reflection of the laser in the optical waveguide.

11. A collimating lens (mainly for fast axis collimation) is disposed in front of the semiconductor lasers to narrow the divergence angle, and the optical waveguide can restrict the laser divergence along the slow axis. In the end, strip spots are produced at the outlet of the optical waveguide, and the energy density of each spot satisfies the requirement for laser medical treatment. Only by a single scanning can the same or even better effect be achieved compared to conventional repeated exposure in the uniform spots. Optionally, a pair of light barriers perpendicular to the slow axis are disposed in front of the light emitting surface of the semiconductor laser to restrict the beams along the slow axis.

Figure 3:
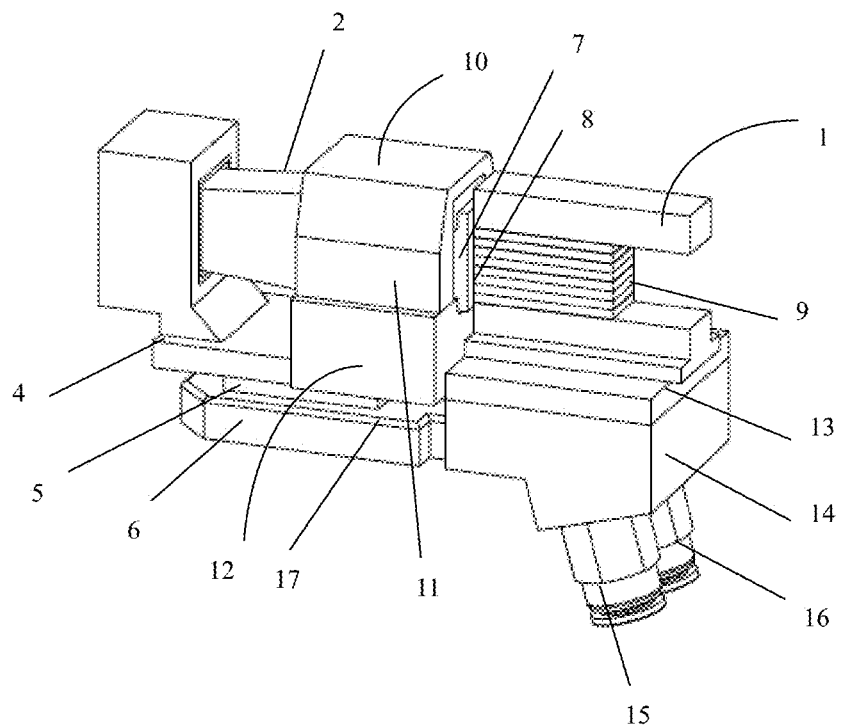
FIG. 3 is a schematic diagram of a semiconductor laser system for medical cosmetology based on the principle of FIG. 2; 1- Semiconductor laser array; 2-Optical waveguide (or light barrier); 4-Cooling window; 5-Thermoelectric cooler (TEC) ; 6-First water throughflow block; 7-Bar chip; 8-Heat sink; 9-Collimating lens; 10-First fixed block; 11-Second fixed block; 12-Thermal insulation cover; 13-Insulation layer; 14-Second water throughflow block; 15-Water inlet; 16-Water outlet; 17-Hollow sleeve.
Figure 4:
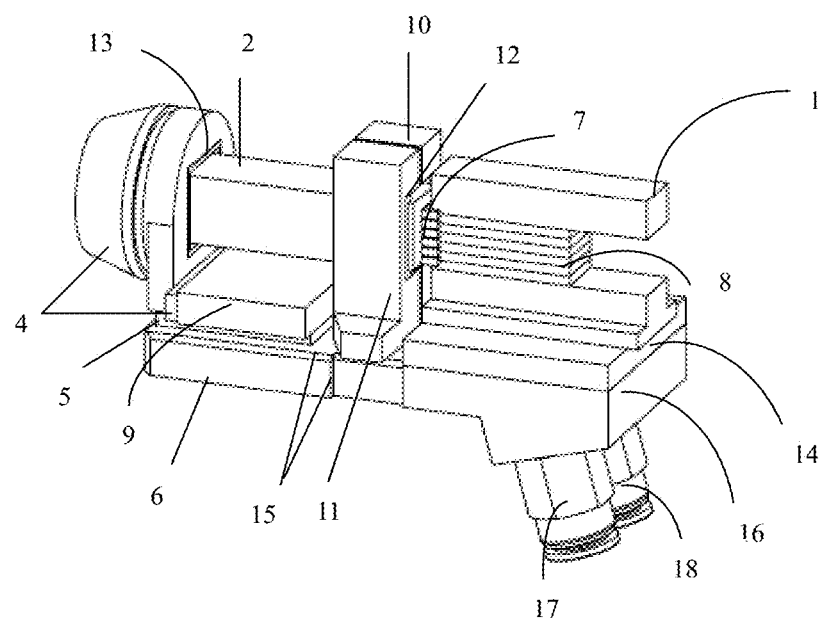
FIG. 4 is a schematic diagram of another semiconductor laser system for medical cosmetology based on the principle of FIG. 2; 1-Semiconductor laser array; 2-Optical waveguide; 3-Contact window; 4-Cooling window; 5-Thermoelectric cooler (TEC); 6-First water throughflow block; 7-Bar chip; 8-Heat sink; 9-Thermal insulation cover; 10-First fixed block; 11-Second fixed block; 12-Pad; 13-Hollow sleeve; 14-Insulation layer; 15-Guide channel; 16-Second water throughflow block; 17-Water inlet; 18-Water outlet.

It is can be seen that the shape of the head of the cooling block and the fixed mode of the optical waveguide in FIG. 4 are different from that in FIG. 3.

Figure 5:
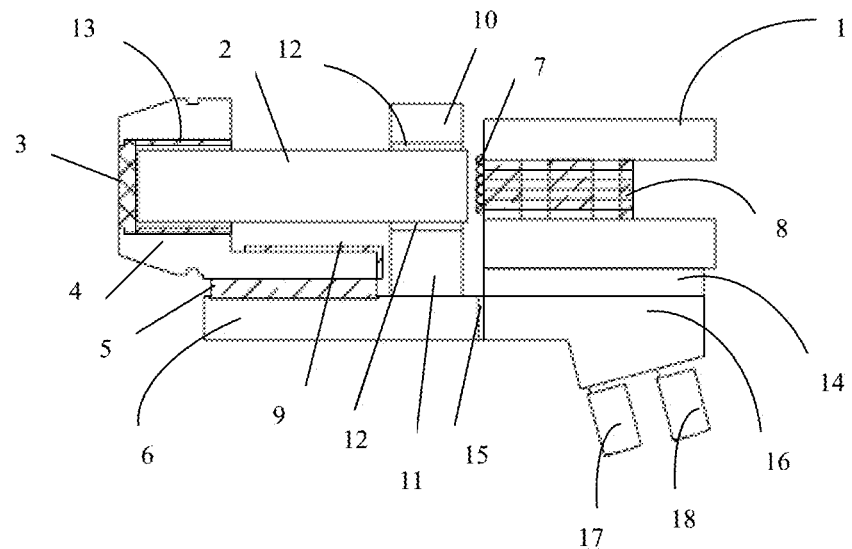

FIG. 5 is a simplified sectional view of FIG. 4; 1-Semiconductor laser array; 2-Optical waveguide; 4-Cooling window; 5- Thermoelectric cooler; 6-First water throughflow block; 7-Collimating lens; 8-Heat sink; 10-First fixed block; 11-Second fixed block; 12-Pad; 13-Hollow sleeve; 14-Insulation layer; 15-Guide channel; 16-Second water throughflow block; 17-Water inlet; 18-Water outlet.

Figure 6:
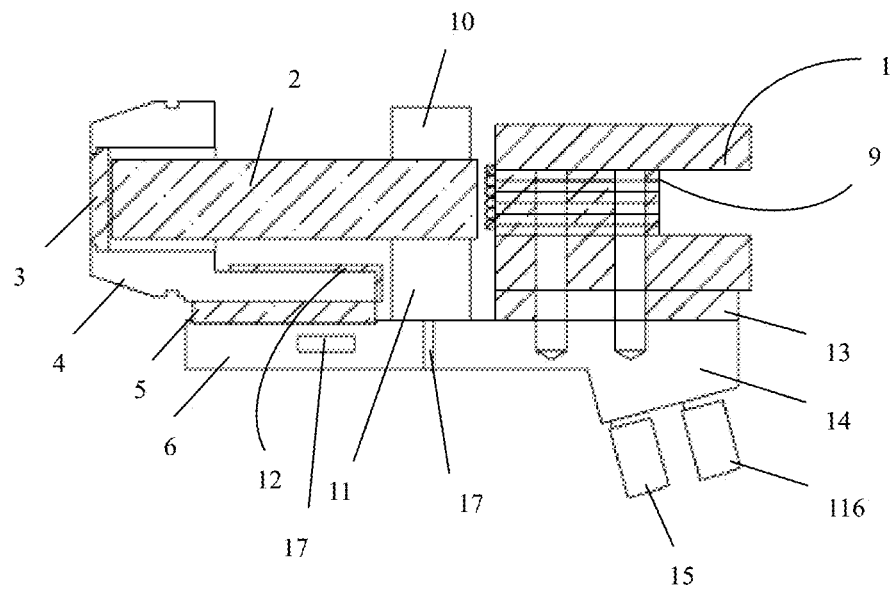

FIG. 6 is a schematic diagram of a semiconductor laser system for medical cosmetology which comprises light barriers instead of an optical waveguide; 1-Semiconductor laser array; 2-Light barrier; 3-Contact window; 4-Cooling window; 5-Thermoelectric cooler (TEC); 6-First water throughflow block; 7-Collimating lens; 8-Heat sink; 9-Thermal insulation cover; 10-First fixed block; 11-Second fixed block; 12-Guide channel; 13-Insulation layer; 14-Second water throughflow block; 15-Water inlet; 16-Water outlet.

Figure 7:
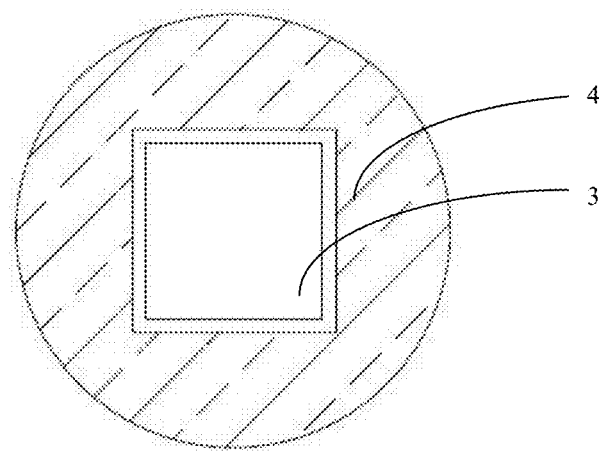

FIG. 7 is a sectional view of a combination of a contact window and a cooling block; 3-Contact window; 4-Cooling window.

Figure 8:
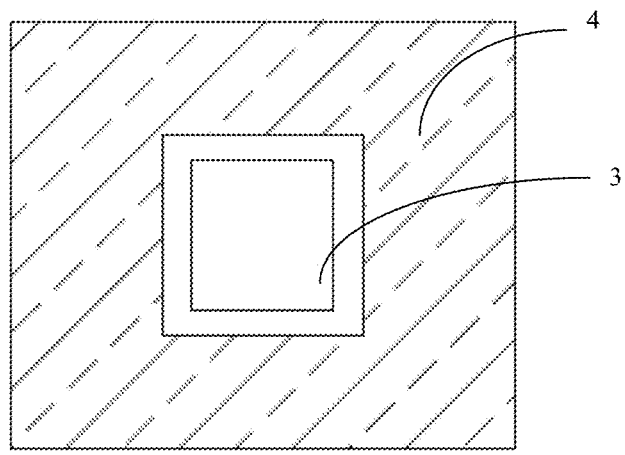

FIG. 8 is a sectional view of another type of combination of a contact window and a cooling block; 3-Contact window; 4-Cooling window.

Figure 9:
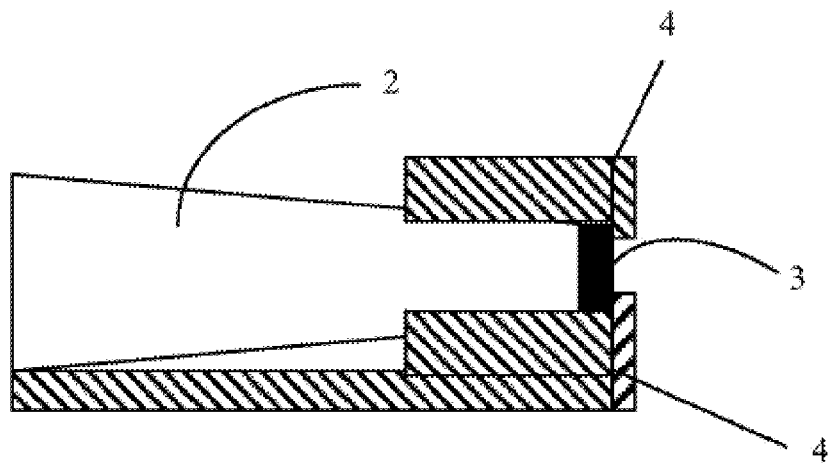

FIG. 9 is an installation diagram of a contact window and a cooling block in the prior art; 2-Optical waveguide; 3-Contact window; 4-Cooling window.

Figure 10:
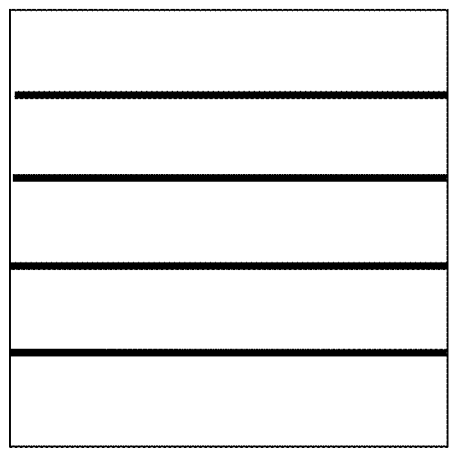

FIG. 10 is a schematic diagram of strip spots in accordance with one embodiment of the invention.

DETAILED DESCRIPTION OF THE EMBODIMENTS

Detailed description of the invention will be given below in conjunction with accompanying drawings.

Figure 1:
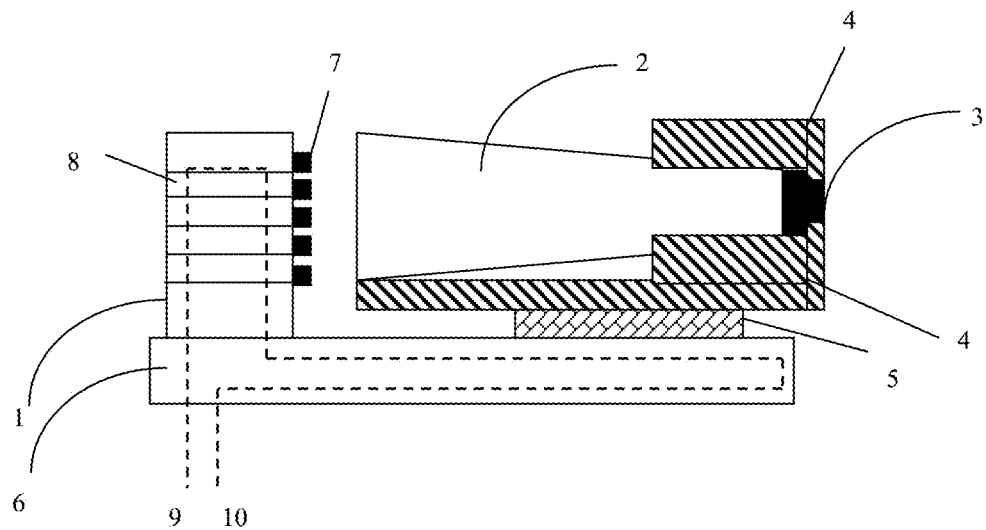
FIG. 1 is a simplified diagram of a semiconductor laser system for medical cosmetology in accordance with one embodiment of the invention; 1-Semiconductor laser array; 2-Optical waveguide; 3-Contact window; 4-Cooling window; 5-Thermoelectric cooler (TEC); 6-Water throughflow block; 7-Bar chip; 8-Heat sink; 9-Water inlet; 10-Water outlet.

As shown in FIG. 1, each bar chip is welded on a heat sink to form a single bar laser. The semiconductor laser array 1 comprises a plurality of stacked single bar lasers, so that the output power of the semiconductor laser array exceeds 200 W.

The optical waveguide 2 is disposed at the light emitting end of the semiconductor laser array 1, totally reflecting and outputting the laser beams. The space between the optical waveguide and the light emitting surface of the semiconductor laser array is between 0.5 and 5.0 mm. Most of the laser energy is constrained and transmitted in the optical waveguide and cannot spill over. In practice, if the optical waveguide is a metal, it should be hollow, and the four inner sides thereof should be plated with reflective films. Optionally, the optical waveguide can be made of transparent material, such as glass, resin, sapphire and diamond, which can be solid or hollow. To improve the energy density, the optical waveguide 2 presents in the form of a frustum of a prism or a frustum of a cone with capacity of beam convergence.

The contact window 3 abuts against a light outlet end of the optical waveguide 2. The contact window 3 is convex, and the bulge of the convex contact window directly contacts the skin. The contact window 3 is made of transparent material with high thermal conductivity, such as sapphire, K9 glass, quartz glass or diamond; the optical waveguide is made of sapphire, K9 glass, or diamond. Preferably, the contact window and the optical waveguide are an integrated structure of sapphire or diamond.

The head of the cooling block cools contact window so that the temperature of the contact window 3 is rather low, thereby not burning the skin. The cooling block comprises a base and a hollow head located on the base. The hollow head tightly abuts against the rear end surface of the contact window (the base and the hollow head are integrated).

A thermoelectric cooler (TEC) 5 is disposed below the base of the cooling block. Water throughflow blocks 6 are disposed below the thermoelectric cooler and below the semiconductor laser array. The water throughflow blocks are made of copper, aluminum, stainless steel, hard anodized aluminum or plastic. The optical waveguide is clamped and fixed on the base of the cooling block 4 or on the water throughflow blocks 6. The hollow head of the cooling block matches the optical waveguide in shape whereby ensuring the maximum area of the hollow head to contact the rear end surface of the contact window, and there is a gap between the hollow head and the optical waveguide. The tail of the cooling block 4 can be suspended below the optical waveguide so that the cooling block does not contact the waveguide 2.

The cooling block 4 is made of high-thermal conductivity material such as copper or aluminum. The thermoelectric cooler 5 is disposed below the cooling block 4 to cool the cooling block 4. The water throughflow blocks disposed below the thermoelectric cooler 5 and the semiconductor laser array 1 are integrated (as shown in FIG. 4, the first water throughflow block and the second water throughflow block). The two water throughflow blocks corresponding to the semiconductor laser array 1 and the thermoelectric cooler (TEC) 5 respectively are connected in series. In the water throughflow block 6, water flows in from the water inlet (the dotted line shows the water flow), passes through the semiconductor laser array 1, reaches the water throughflow blocks, and flows out from the water outlet.

The optical waveguide reshapes the large spot from the semiconductor laser array into uniform small spots. The divergence angle of the bars along the fast axis in the semiconductor laser array is between 30 and 49 degrees. The beams are reflected repeatedly in the optical waveguide to form uniform light spots in the end.

If the optical waveguide 2 presents in the form of a frustum of a prism or a frustum of a cone with capacity of beam convergence, the laser spot from the semiconductor laser array 1 converges to a very small size at the light outlet of the optical waveguide, so that the energy density is enhanced and can meet the requirement for laser medical treatment such as hair removal or cosmetology. The laser directly acts on the skin via the contact window 3.

To alleviate pain, the cooling source of the contact window is a thermoelectric cooler (TEC), the hot end of which is connected to the water throughflow block, and the cold end of which is connected to the cooling block. Through the thermal conduction, the cooling path is from the thermoelectric cooler (TEC) to the cooling block, then to the contact window, and finally to the skin, which protects the skin from damage. In use, the contact window close contacts the skin, and the temperature of the contact site is close to degrees Celsuis, which effectively protects the skin from heat injury and pain, and increases the treatment energy and improves the therapeutic effectiveness. In use, the contact window presses the skin and flattens the hair follicle, so that the absorption rate of the laser is increased by 30-40%.

Figure 2:
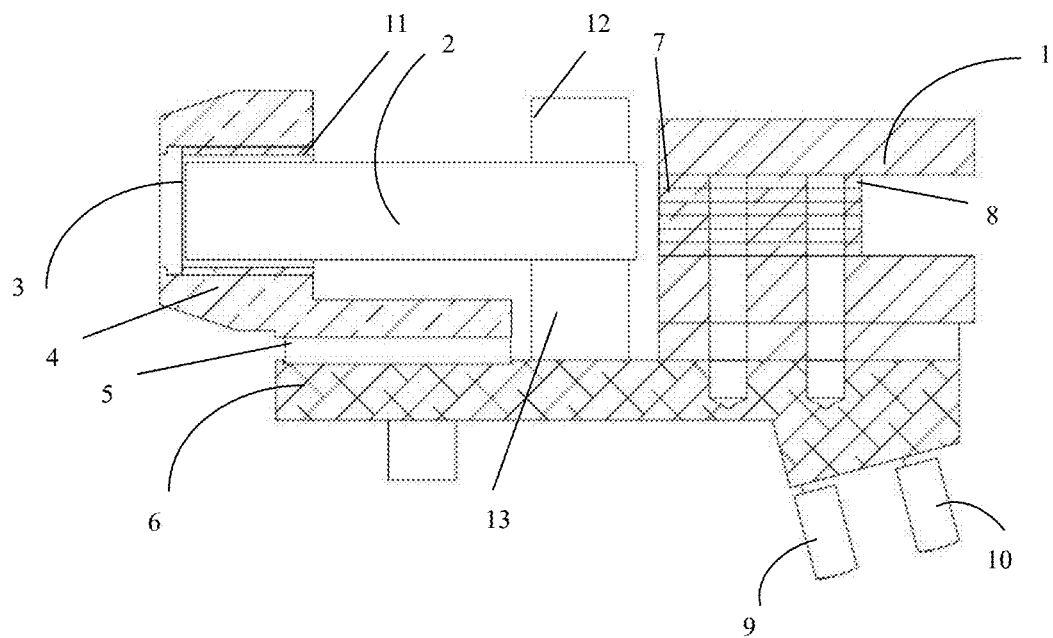
FIG. 2 is a schematic diagram of a semiconductor laser system comprising a hollow sleeve; 1-Semiconductor laser array; 2-Optical waveguide; 3-Contact window; 4-Cooling window; 5-Thermoelectric cooler (TEC); 6- Water throughflow block; 7-Bar chip; 8-Heat sink; 9-Water inlet; 10-Water outlet; 11-Hollow sleeve; 12-First fixed block; 13-Second fixed block.

As shown in FIG. 2, the semiconductor laser system for medical cosmetology in FIG. 1 is updated. The cooling block comprises a base and a hollow head located on the base. The forepart of the hollow head abuts against and tightly clasps side walls of the contact window. A hollow sleeve is fixed in the cavity of the hollow head. The hollow sleeve is connected to and fixed on the inner wall of the hollow head through point contact. The front end of the hollow sleeve abuts against a rear end surface of the contact window. The light outlet end of the optical waveguide is located in the hollow sleeve. A gap is provided between the light outlet end of the optical waveguide and the hollow sleeve.

A thermal insulation cover is disposed to cover the base of the cooling block.

The guide channel is provided on the base of the cooling block and/or the surface of the first water throughflow block to guide excess water to discharge.

As shown in FIG. 3, the optical waveguide is fixed at the top by a first fixed block 11 and at the side by a second fixed block 12. Optionally, as shown in FIG. 4, the optical waveguide can also be clamped and fixed using a pair of trough type fixed blocks disposed on the base of the cooling block or on the first water throughflow block. The pair of trough type fixed blocks are fixed by a through bolt.

The contact surface of the optical waveguide and the fixed blocks is provided with a pad comprising a hollow center. The pad is a filler ring, or a structure with a cross section being a polygon frame or elliptical frame. Preferably, the pad is made of flexible material such as polyoxymethylene, polyethylene, polystyrene, polypropylene, polyamide or vulcanized rubber.

As shown in FIGS. 3 and 5, as needed, a collimating lens is disposed in front of the semiconductor lasers for fast axis collimation or for fast and slow axis collimation simultaneously. The collimating lens is a miniature collimating lens disposed on a bar chip of each laser of the semiconductor laser array; or the collimating lens is an integrated structure disposed in front of the semiconductor laser array. In the end, strip spots are formed in the outlet of the optical waveguide (as shown in FIG. 10). Only by a single scanning can the same or even better effect be achieved compared to conventional repeated exposure in the uniform spots.

In the presence of the collimating lens, as shown in FIG. 6, the optical waveguide can be replaced by a pair of light barriers which are perpendicular to the slow axis and are plated with high-reflective films on inner sides thereof, so that the divergence from the slow axis is prevented. The light barriers are made of gold-plated copper or silver-plated copper. The pair of light barriers is inserted and fixed on the base of the cooling block or a slot preset on the first water throughflow block. The light outlet end of the pair of light barriers is located in the cavity of the hollow head, and a gap is provided between the light outlet end of the light barriers and the inner wall of the hollow head; and the transparent convex contact window is disposed in front of the light outlet end of the light barriers.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A semiconductor laser system for medical cosmetology, comprising:
a semiconductor laser array comprising a plurality of stacked semiconductor lasers,
an optical waveguide disposed in front of a light emitting surface of the semiconductor laser array,
a transparent convex contact window disposed in front of a light outlet end of the optical waveguide, and
a cooling block for conduction cooling of the contact window;
wherein the cooling block comprises a base and a hollow head located on the base; a forepart of the hollow head abuts against and tightly clasps side walls of the contact window; the light outlet end of the optical waveguide is located in a cavity of the hollow head, and a gap is provided between the light outlet end of the optical waveguide and an inner wall of the hollow head;
a thermoelectric cooler is disposed below the base of the cooling block; a first water throughflow block is disposed below the thermoelectric cooler; and a second water throughflow block is disposed below the semiconductor laser array.

2. The system of claim 1, wherein
a hollow sleeve comprising a high reflection film-coated inner surface is fixed in the cavity of the hollow head; the hollow sleeve is connected to and fixed on the inner wall of the hollow head through point contact; a front end of the hollow sleeve abuts against a rear end surface of the contact window; the light outlet end of the optical waveguide is located in the hollow sleeve; and a gap is provided between the light outlet end of the optical waveguide and the hollow sleeve.

3. The system of claim 2, wherein the hollow sleeve is made of copper and the high reflection film is gold-plated or silver-plated.

4. The system of claim 1, wherein the optical waveguide is clamped and fixed using a pair of trough type fixed blocks disposed on the base of the cooling block or on the first water throughflow block; the pair of trough type fixed blocks are fixed by a through bolt; and a contact surface of the optical waveguide and the fixed blocks is provided with a flexible pad comprising a hollow center.

5. The system of claim 1, wherein an insulation layer is disposed at a bottom of the semiconductor laser array, and the semiconductor laser array is fixed on the second water throughflow block via the insulation layer.

6. The system of claim 1, wherein a thermal insulation cover is disposed to cover the base of the cooling block.

7. The system of claim 1, wherein a guide channel is provided on the base of the cooling block and/or a surface of the first water throughflow block to guide excess water to discharge.

8. The system of claim 1, wherein liquid cooling channels of the first water throughflow block and the second water throughflow block are connected in series or are independent from each other.

9. The system of claim 1, wherein the optical waveguide as a whole is a cylinder, a frustum of a cone, a prism, or a frustum of a prism.

10. The system of claim 1, wherein a space between the optical waveguide and the light emitting surface of the semiconductor laser array is between 0.5 and 5.0 mm.

11. The system of claim 1, wherein the contact window is made of sapphire, K9 glass, quartz glass or diamond; the optical waveguide is made of sapphire, K9 glass, or diamond.

12. The system of claim 11, wherein the contact window and the optical waveguide are an integrated structure of sapphire or diamond.

13. The system of claim 1, wherein the cooling block is made of copper, aluminum, iron, gold-plated copper, gold-plated aluminum, stainless steel or diamond.

14. The system of claim 1, wherein the first water throughflow block and the second water throughflow block are made of copper, aluminum, stainless steel, hard anodized aluminum or plastic.

15. The system of claim 1, wherein the semiconductor lasers each comprise bar chips packaged on a heat sink, and the heat sink is a micro-channel heat sink, a macro-channel heat sink or a metal block; the bar chips comprise a single luminous point or a plurality of luminous points.

16. The system of claim 1, wherein a collimating lens is disposed in front of the semiconductor lasers for fast axis collimation or for fast and slow axis collimation simultaneously.

17. The system of claim 16, wherein the collimating lens is a miniature collimating lens disposed on a bar chip of each laser of the semiconductor laser array; or the collimating lens is an integrated structure disposed in front of the semiconductor laser array.

18. The system of claim 16, wherein the optical waveguide is replaced by a pair of light barriers which are perpendicular to the slow axis and are plated with high-reflective films on inner sides thereof; the pair of light barriers is inserted and fixed on the base of the cooling block or a slot preset on the first water throughflow block; a light outlet end of the pair of light barriers is located in the cavity of the hollow head, and a gap is provided between the light outlet end of the light barriers and the inner wall of the hollow head; and the transparent convex contact window is disposed in front of the light outlet end of the light barriers.

19. The system of claim 18, wherein the light barriers are made of gold-plated copper or silver-plated copper.

* * * * *